United States Patent [19]

Harada: Yoshimichi et al.

[11] Patent Number: 4,936,980
[45] Date of Patent: Jun. 26, 1990

[54] APPARATUS AND METHOD FOR PLASMA SEPARATION

[75] Inventors: Harada: Yoshimichi, Fukushima; Kenji Kubota, Okayama; Yasuzo Kirita, Toyonaka; Tadayuki Yamane, Kyoto, all of Japan

[73] Assignee: Kuraray Co., Ltd., Kurashiki, Japan

[21] Appl. No.: 224,899

[22] Filed: Jul. 27, 1988

Related U.S. Application Data

[63] Continuation-in-part of Ser. No. 492,746, May 5, 1983, abandoned.

[30] Foreign Application Priority Data

May 28, 1982 [JP] Japan ..................... 57-91803

[51] Int. Cl.⁵ .......................... B01D 13/00
[52] U.S. Cl. ..................... 210/647; 210/90; 210/651; 210/321.65
[58] Field of Search ............ 210/90, 321.65, 647, 210/651

[56] References Cited

U.S. PATENT DOCUMENTS

4,202,764  5/1980  Afflerbaugh et al. ............... 210/647
4,370,983  2/1983  Lichtenstein .................. 210/321.65

*Primary Examiner*—Frank Spear
*Attorney, Agent, or Firm*—Kramer, Brufsky, & Cifelli

[57] ABSTRACT

The invention provides an apparatus and method for plasma separation which is designed so that during the process of separating blood into plasma and corpuscular components by means of plasma separation membranes, if the rate of plasma permeation through the membranes is decreased so that the trans-membrane pressure differential exceeds a predetermined value, the number of revolutions of a plasma pump is adjusted downward to permit restoration of a trans-membrane pressure differential lower than the predetermined value. The rate of plasma discharge is gradually decreased according to the varying permeability of the membranes to plasma, whereby a most effective performance of the membranes can be assured. The apparatus and method can be employed in practicing various blood treatment methods wherein blood is separated into plasma and corpuscular fractions to remove the plasma containing pathogenic factors or to remove the pathogenic factors from the plasma.

23 Claims, 4 Drawing Sheets

APPARATUS AND METHOD FOR PLASMA SEPARATION

RELATED APPLICATIONS

This application is a continuation-in-part of now abandoned U.S. patent application Ser. No. 492,746, filed May 5, 1983.

BACKGROUND OF THE INVENTION

1. Field of the Invention

The present invention relates to a plasma separation apparatus and method adapted for effectively separating blood into plasma and corpuscular components including red and white corpuscles and elementary particles by using plasma separation membranes.

2. Description of Prior Art

Various blood treatment techniques such as hemodialysis using a dialysis membrane, hemofiltration with a filtration membrane and hemoperfusion with an adsorbent, among others, have come into wide clinical use. Recently, a technique called plasmapheresis, which is one of the extracorporeal blood treatment techniques, has been developed. Said plasmapheresis comprises first separating blood into plasma and corpuscular components and then treating the plasma by a certain technique, thereby removing pathogenic factors Among various plasmapheresis methods which have been proposed to date are:

(1) a method wherein blood is separated into plasma and corpuscular components through plasma separation membranes and then the plasma fraction containing pathogenic factors is discharged, the corpuscular fraction being returned to the circulation as it is or together with a plasma preparation in the same amount as the discharged plasma fraction;

(2) a method wherein blood is separated into plasma and corpuscular components through plasma separation membranes, then the plasma fraction containing pathogenic factors are brought into contact with an adsorbent so that the pathogenic factors are removed by adsorption, and subsequently said plasma fraction is mixed with the corpuscular fraction for return to the circulation (as disclosed in U.S. Pat. Nos. 4,013,564 and 4,243,532, for example);

(3) a method wherein from blood diluted with a plasma preparation is removed by separation through plasma separation membranes a plasma fraction equivalent to the quantity of the plasma preparation used for said dilution, the corpuscular components only of the blood being returned to the circulation;

(4) a method wherein blood is separated into plasma and corpuscular components through plasma separation membranes, then the plasma is further fractionated into a low-molecular-weight fraction and a high-molecular-weight fraction by means of plasma treatment membranes, so that the high-molecular-weight fraction, which contains pathogenic factors, is removed and the low-molecular-weight fraction is mixed with the corpuscular components for return to the circulation (as disclosed in U.S. Pat. No. 4,350,594, for example); and (5) a method wherein blood is separated into plasma and corpuscular components through plasma separation membranes, then the plasma is cooled so that its high-molecular-weight component is allowed to gel, and the gel is removed through a filtration membrane, a low-molecular-weight fraction passed through the filtration membrane being mixed with the corpuscular component for return to the circulation (as disclosed in Artificial Organs Vol. 4, No. 3, pp. 205–207, June 1980, for example). To practice any of these methods, it is essential that blood should be efficiently separated into plasma and corpuscular components. Further teachings have already been made available on such separation methods and apparatuses therefor. For example, a Japanese patent application laid open under No. 110625/1981 discloses a method and apparatus wherein membranes having a pore diameter of $0.1$–$0.6\mu$ are used to separate plasma from blood, with the trans-membrane pressure difference kept within a range of 50 mmHg–10 mmHg, so that the rate of plasma separation may be improved. Another Japanese patent application, laid open under No. 105707/1981 discloses a plasma separation apparatus such that if the trans-membrane pressure difference exceeds a predetermined value, the plasma pump is stopped and if the trans-membrane pressure difference regains the predetermined value, the pump is operated. However, these teachings are no more than proposals of possibilities or theoretical apparatus.

These techniques are such that the plasma discharge pump is ON-OFF controlled to prevent any abnormal increase in trans-membrane pressure differential, and therefore, once the plasma permeation performance of the membranes drops, it is necessary that the plasma pump should be subjected to frequent ON-OFF control. However, frequent ON-OFF manipulation of the plasma involves a difficulty in that at the instant the pump is actuated, the trans-membrane pressure differential may become excessively large, or the plasma discharge pressure may become negative, thus there being an increased chance of the corpuscular components of the blood being destroyed.

Prior to the development of the present invention, apparatus for plasma separation using plasma separation membranes suffered from several practical disadvantages which had limited their commercial exploitation. In particular, hitherto proposed apparatus incorporating plasma separation membranes were susceptible to at least three disadvantages; namely:

Hemolysis, that is the rupture or lysis of cells in the corpuscular component, was a significant problem. The semipermeable membranes used in plasma separators are intended to allow the plasma fraction of the blood to pass therethrough. As such, they have a larger pore size as compared to, for example, membranes used in blood dialysis apparatus. The result is that the cells of the corpuscular components of the blood being retained by the membranes, are very susceptible to hemolysis when the transmembrane pressure exceeds a certain level. To prevent hemolysis, it is therefore very important to ensure that the transmembrane pressure in the plasma separation apparatus does not exceed this certain level.

At the start of a plasma separation treatment for a patient, the passage of the plasma through the membrane of the separator causes the cells of the corpuscular blood components to be drawn to the surface of the membrane where they tend to accumulate. This in turn causes the pores of the membrane to become clogged with deposited cells so that the passage of plasma through the membrane becomes increasingly more difficult. The result is an increase in transmembrane pressure as the treatment of the patient progresses. This phenomenon is especially aggravated if the rate of plasma separation at the start of treatment is high, since the pores become quickly and irreversibly clogged. Not only does this mean that the rate of plasma withdrawn from the patient decreases quickly during treatment, but the increased transmembrane pressure due to clogging may cause an increased chance of hemolysis.

On commencing a plasma treatment process for a patient, the membrane is free of clogging cells so that the rate of separation of plasma from the blood is very high. This means that the amount of blood returned to the patient during the initial treatment phase is very low and can give rise to serious medical problems in the treatment of the patient.

U.S. Pat. No. 4,191,182 to Popovich et al. discloses a continuous plasmapheresis system employing ultrafiltration with a membrane to separate blood into plasma and cellular components. Popovich et al. also addresses the problem of preventing the membrane from clogging. For example, "(o)ne of these problems is that the flow rates must be controlled fairly closely. Thus, if the flow rate employed is too fast, turbulence will occur within the ultrafiltration cell which may cause hemolysis and the general destruction of cellular components. On the other hand, if flow rates and transmembrane pressures are not controlled adequately the cellular and macro-molecular components of the blood will tend to clog up the membrane thus significantly slowing the ultrafiltration rate. Such clogging can also cause hemolysis to occur." Further, "Continuous plasmapheresis is accomplished by continually withdrawing whole blood from a blood vessel and pumping same through an ultrafiltration chamber to effect separation of plasma and cellular components. The blood passes in laminar flow, parallel to the plane of the ultrafiltration membrane at flow rates sufficient to create shear stress across the ultrafilter membrane of from about 10 dynes/cm$^2$ to about 1000 dynes/cm$^2$."

An important distinction between the apparatus disclosed in Popovich et al. and the present invention is that the former is operated so that the pressure in the filtrate chamber is kept constant in order for the flow rate across the filtering side of the membrane to be kept constant, while the latter is operated so that the pressure in the filtrate chamber is varied in order that the pressure across the membrane is kept constant. As stated in the disclosure of Popovich et al., "the rate at which plasma pump 29 operates can be controlled such that the pressure in plasma outlet conduit 23 never varies from that necessary to maintain optimum transmembrane pressure regardless of the rate of ultrafiltration. Preferably the pressure in filtrate chamber 9b is kept at about atmospheric pressure at all times."

To illustrate the advantage of the present invention over the apparatus and method disclosed in the Popovich et al. patent, an experiment was conducted using a plasma separator built into the circuit shown in FIG. 4 herein. The same separator was also built into the circuit shown in FIG. 1 of the Popovich et al. patent.

The plasma separator was constructed by incorporating into a cylindrical cartridge a polyvinyl alcohol hollow fiber membrane having a substantially uniform microporous structure with an average pore size of 0.2 micron, an inside diameter of 330 microns, a membrane thickness of 125 microns and the membrane area being 0.5 m$^2$.

With the plasma separator built into the circuit shown in FIG. 4 herein, the blood of a patient was treated. For plasma separation, the blood flow rate through blood pump was adjusted to 120 milliliters per minute (ml/mn). Concurrently, the plasma pump speed value was preset to 30 ml/min with the plasma pump speed setting circuit, and the value of the transmembrane pressure differential was set to 50 millimeters of mercury (mmHg) by the setting circuit. The transmembrane pressure differential was kept within 50 mmHg by gradually decreasing the rate of plasma discharge according to the degree of membrane clogging. With this method, the patient's blood was continuously treated for two hours. During that time, about 3.5 liters of fresh frozen plasma was pumped into the patient and about 3.5 liters of plasma was separated from the patient.

The same plasma separator was then built into the circuit shown in FIG. 1 of the Popovich et al. reference and the blood of the patient was treated. For plasma separation, the blood flow rate through the blood pump was adjusted to 120 ml/min, and the blood recycle pump speed value was set to 300 ml/min. The plasma pump speed was gradually decreased for maintaining the pressure in plasma outlet conduit at 0 mmHg. In addition, the plasma pump and the fresh frozen plasma pump were controlled in association with each other. The rate of flow of separated plasma was about 50 ml/min at the beginning but rapidly dropped with the lapse of time. In this manner, the blood was treated continuously for two hours. During this time, 2.8 liters of fresh frozen plasma was pumped into the patient and 2.8 liters of plasma was separated from the patient. It is noteworthy that the magnitude of a second pressure sensor at the outlet conduit randomly fluctuated during the treatment process within a range of about 50 mmHg to 135 mmHg when a resistance was provided at the outlet conduit due to the blood pressure of the patient connected to the apparatus.

This experiment illustrates the advantage, i.e., increased volume of plasma operation, of maintaining the transmembrane pressure constant in accordance with the present invention as compared with maintaining the flow rate constant in accordance with the disclosure of Popovich et al.

SUMMARY OF THE INVENTION

Accordingly it is an object of the present invention to provide a plasma separation apparatus and process which permits effective plasma separation without destroying the corpuscular components of the blood.

It is another object of the invention to provide a plasma separation apparatus and process such that if corpuscles in the blood deposit on the surface of the plasma separation membranes to gradually lower the permeability of the membranes to plasma, with the result of increased transmembrane pressure differential, the membranes are allowed to satisfactorily exhibit the performance characteristics thereof by decreasing the rate of plasma permeation according to the decreased membrane permeability to plasma and without stopping the plasma pump, thereby lowering the trans-membrane pressure differential.

It is a further object of the invention to provide a plasma separation apparatus and process which makes it possible to control the trans-membrane pressure differential and plasma discharge pressure within such limits that will never destroy corpuscular components.

Thus, the present invention provides an apparatus and process for plasma separation comprising a blood transfer tube, a plasma separator connected to said transfer tube and incorporating membranes adapted to continuously separate blood into plasma and corpuscular components, a plasma pump for discharging plasma from said plasma separator, means for detecting trans-membrane pressure differentials in said plasma separator, a comparator circuit for comparing detected trans-membrane pressure differential with a predetermined value for such differential, a pulse generating circuit for producing pulses if said detected value is greater than said predetermined value, a voltage or pulse conversion circuit for converting said pulse into a voltage value or digital pulse value and transmitting such value as a plasma-pump speed drop signal, and a subtraction circuit for performing subtracting operation as to said speed drop signal relative to a speed setting signal for said plasma pump and for transmitting the difference as a speed control signal for the pump, whereby the number of revolutions of the plasma pump is lowered to adjust the trans-membrane pressure differential if the detected trans-membrane pressure differential is greater than the predetermined pressure.

The pump speed value preset in the plasma speed setting circuit will generally be chosen at a value below a value corresponding to the maximum plasma discharge rate for a new membrane in the apparatus. This ensures that the initial rate of plasma discharge, (i.e. before substantial clogging of the membrane takes place), is not too high and thereby reduces the danger to the patient of too little blood being returned during the initial phase of treatment. As the treatment process progresses, the rate of plasma discharge will remain constant at a level which will ensure that membrane clogging occurs relatively slowly. However, the membrane will eventually be clogged whereupon the trans-membrane pressure will exceed a predetermined value, which predetermined value can be set according to the optimum characteristics of the membrane The time before the onset of clogging will however be substantially longer than for the prior art apparatus. When clogging does take place, the pulse generating circuit produces pulses which are integrated and converted into an analog plasma-pump speed drop signal. This speed drop signal is then subtracted from the preset speed value for the plasma pump to give a speed control signal for the pump. In this way, the speed of the pump and thus the rate of plasma discharge, is gradually decreased according to the degree of clogging of the separation membrane. In this way, hemolysis in the separator is substantially prevented.

DETAILED DESCRIPTION OF THE INVENTION

Figure 1:
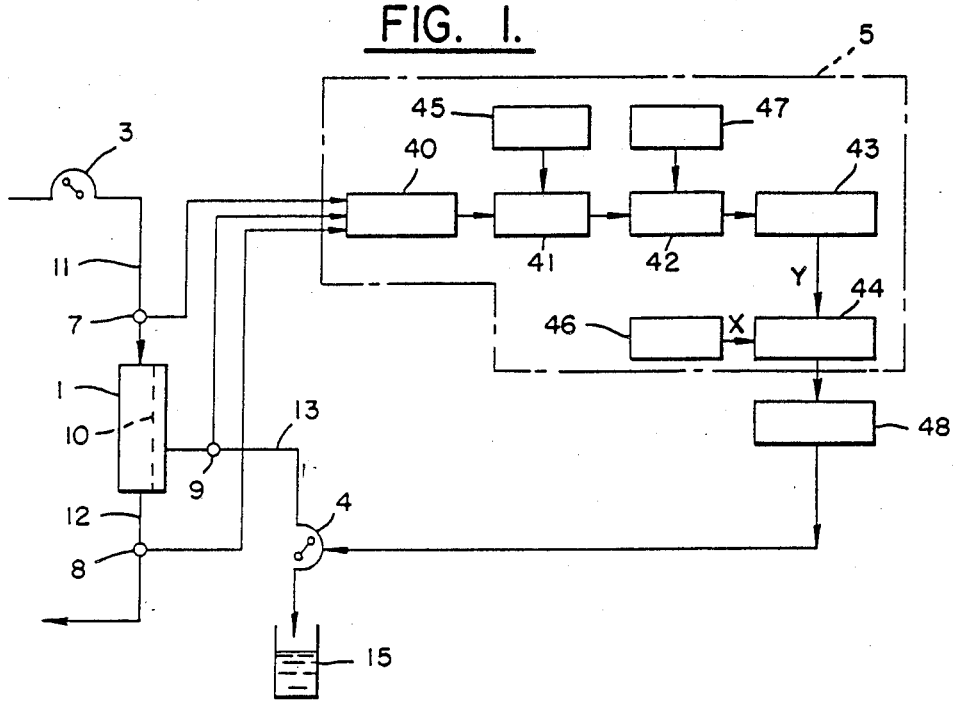
FIG. 1 is an electric circuit diagram representing the apparatus according to the present invention.

FIG. 1 is a block schematic diagram showing an apparatus according to the invention. The apparatus comprises a plasma separator 1 incorporating plasma separation membranes 10, a plasma pump 4, and a circuit 5 for controlling trans-membrane pressure differentials. The plasma separator 1 for separating blood into plasma and corpuscular components has membranes 10 of hollow fiber or flat membrane form incorporated therein Each plasma membrane has a pore size of about 0.02 to about 0.4μ, or preferably about 0.1μ. Preferably, this membrane will be a homogeneous microporous membrane, a microfiltration membrane or a so-called asymmetrical membrane comprising a porous supporting layer and a relatively dense microporous layer.

Examples of such membranes are substantially uniform microporous membranes made of polyvinyl alcohol (PVA) type polymers, as well as other substantially uniform microporous membranes and asymmetrical membranes made of ethylene-vinyl alcohol (EVA) copolymers, cellulose derivatives such as cellulose acetates, polyolefins, polyacrylonitriles, polyamides, polyesters, polysulfones, and so on. Preferred among these are PVA, EVA, cellulose derivative and polysulfone membranes, which have good biocompatibility.

The plasma separator 1 has an inlet for blood, an outlet for corpuscular components, and an outlet for plasma fraction passed through the membranes. To said inlet and outlets there are connected a blood transfer tube 11, a corpuscular component transfer tube 12, and a plasma transfer tube 13, respectively.

A blood pump 3 is disposed on said blood transfer tube 11 and is adapted to supply blood to said plasma separator 1 at a constant flow rate of about 50 to about 200 ml/min.

A pump 4 is disposed on said plasma transfer tube and is adapted to discharge plasma from the plasma separator.

Blood transfer tube 11, corpuscular component transfer tube 12, and plasma transfer tube 13 have pressure sensors 7, 8 and 9 respectively disposed therein. Each of these sensors is adapted to continuously produce electric signals indicative of proportional changes in pressure. For example, diaphragm displacement is due to pressure, through such means as a strain meter, a semiconductor strain meter, or a Hall effect element.

The circuit 5 for controlling trans-membrane pressure difference comprises a computing unit 40 which computes pressures detected by pressure sensors 7, 8, 9 according to the equation $$P_T = \frac{P_1 + P_2}{2} - P_3, \text{ or } P_T = P_1 - P_3$$

where $P_1$ denotes pressure on the blood inlet side of the plasma separator, $P_2$ denotes pressure on the corpuscular component outlet side of the plasma separator, and $P_3$ denotes plasma discharge pressure in the plasma separator.

A comparator circuit 41 compares the detected trans-membrane pressure differentials with the predetermined value therefor. A pulse generating circuit 42 produces pulses if said detected value is greater than said predetermined value A voltage or pulse conversion circuit 43 converts said pulse into a voltage value, or digital pulse value and transmits such value as a plasma-pump speed drop signal. A subtractor circuit 44 performs a subtracting operation as to said speed drops signal relative to a speed setting signal for said plasma pump and transmits the difference as a speed control signal to the pump.

Said trans-membrane pressure differential is normally set at about 50 to about 100 mmHg.

Figure 2A:
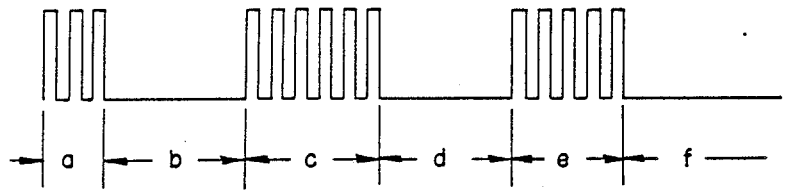
FIGS. 2A, 2B and 2C are diagrammatic illustrations showing variability with time of signals in said circuit.
Figure 2B:
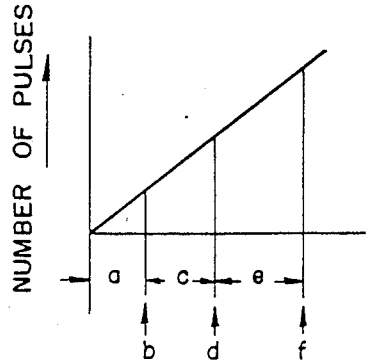
Figure 2C:
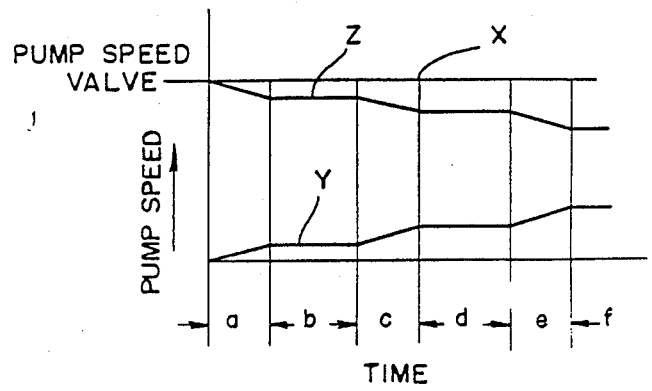

The operation of the apparatus will now be explained with reference to FIGS. 2 and 3. Pumped by the blood pump 3 at a constant flow rate, blood is delivered to the plasma separator 1, where the plasma component of the blood is caused to permeate the membranes and to be discharged by the plasma pump 4. Concurrently, the corpuscular components are returned to the intracorporeal circulation through the corpuscular component transfer tube 12. The quantity of plasma discharged from the plasma separator 1 normally corresponds to a value calculated according to the following equation:

$$Q_2 = \frac{100 - H_t}{100} \times Q_1 \times \frac{1}{2}$$

where $Q_1$ denotes the quantity of blood transferred into the plasma separator, and $H_t$ denotes a hematocrit value (%) of blood If the process of filtration continues in accordance with the conditions as represented by the equation, clogging of the plasma separation membrane gradually develops, thus leading to increased trans-membrane pressure differential. If the trans-membrane pressure difference exceeds the predetermined limit, it is possible that the corpuscular components may be destroyed. Therefore, it is necessary that said trans-membrane pressure differential should be controlled within the predetermined range.

Control of the trans-membrane pressure differential is carried out in the following way. A trans-membrane pressure differential is computed at the computing circuit 40; comparison is made at the comparator circuit 41 to determine whether the pressure differential is higher or lower than the value preset at the setting circuit 45; and if the pressure differential is higher than the preset value, a pulsation start signal is given to the pulse generating circuit 42. Then, pulses are produced at the pulse generating circuit 42 as shown in zones a, c and e in FIG. 2A. The number of pulses generated in said zones a, c, e are integrated at the voltage or pulse conversion circuit 43 for conversion into analog data illustrated in FIG. 2B. The integrated value Y in analog terms from said conversion circuit 43 is subtracted at the subtraction circuit 44 from the pump speed value X preset at the plasma-pump speed setting circuit 46, as can be seen from FIG. 2C. The resulting value Z from the subtraction is given to a drive circuit 48 as a plasma-pump speed control signal.

If the trans-membrane pressure differential is higher than the preset value at the setting circuit 45, the number of revolutions of the plasma pump will drop. But, if the flow rate of the plasma being discharged is decreased, the trans-membrane pressure differential will be lowered accordingly. The number of revolutions of the plasma pump will continue to decrease until a trans-membrane pressure differential which is lower than the value set by the setting circuit is restored (that is, in zones a, c, e). Upon recovery of a trans-membrane pressure differential lower than the preset value, the comparator circuit 41 transmits a stop-pulse signal to the pulse generating circuit 42 to stop pulse generation. While the trans-membrane pressure differential is lower than the preset value (that is, zones b, d, f are maintained), the number of revolutions of the plasma pump is kept at the same level reached when pulse generation has stopped.

Designated as 47 is a pulse frequency setting circuit. The rate of decrease in the number of revolutions of the plasma pump can be adjusted by changing the cycle of pulse generation. Preferably, such rate of decrease should be set slightly larger than the rate of decrease in the plasma passing ability of the plasma separator. It is noted, however, that such setting need not be exaggerated, because there will be no abrupt occurrence of decreases due to time factor in the plasma separating ability of said separator.

Figure 3:
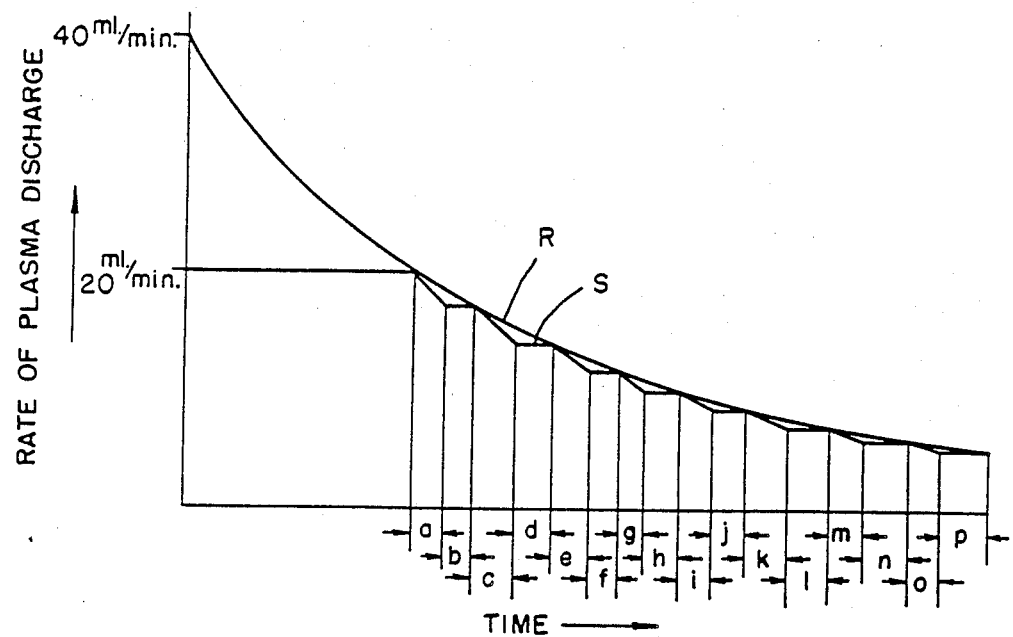
FIG. 3 is an illustration showing the relation between membrane performance and plasma discharge rate where the apparatus of the invention is employed.

FIG. 3 shows the relation between membrane performance and plasma discharge rate. The plasma separation membrane is subject to a gradual decrease in its permeability to plasma due to clogging and other factors during operation. With the apparatus according to the invention, however, it is possible to permit good membrane performance in plasma permeation, with trans-membrane pressure differentials kept within a predetermined range, by gradually decreasing the rate of plasma discharge according to the degree of membrane clogging. That is, the rate of plasma discharge is automatically adjusted according to the membrane performance varying with time. For example, the number of revolutions of the pump is set to about one half of the maximum membrane permeability value (e.g., 40 ml/min × ½ = 20 ml/min). Generally, in the course of the rate of plasma permeation being decreased to one half of the maximum permeation rate, the trans-membrane pressure differential rarely if ever exceeds a 50–100 mmHg range. If the rate of permeation is decreased to less than 20 ml/min due to membrane clogging, the trans-membrane pressure differential will exceed the preset value; therefore, the number of revolutions of the plasma pump is decreased to lower the trans-membrane pressure differential. By repeating this procedure it is possible to gradually decrease the rate of plasma discharge S or the number of revolutions of the plasma pump according to the decreasing membrane permeability R. The shorter the cycle of pulse generation, the more the rate of plasma discharge can be approximated to the membrane permeability.

Figure 4:
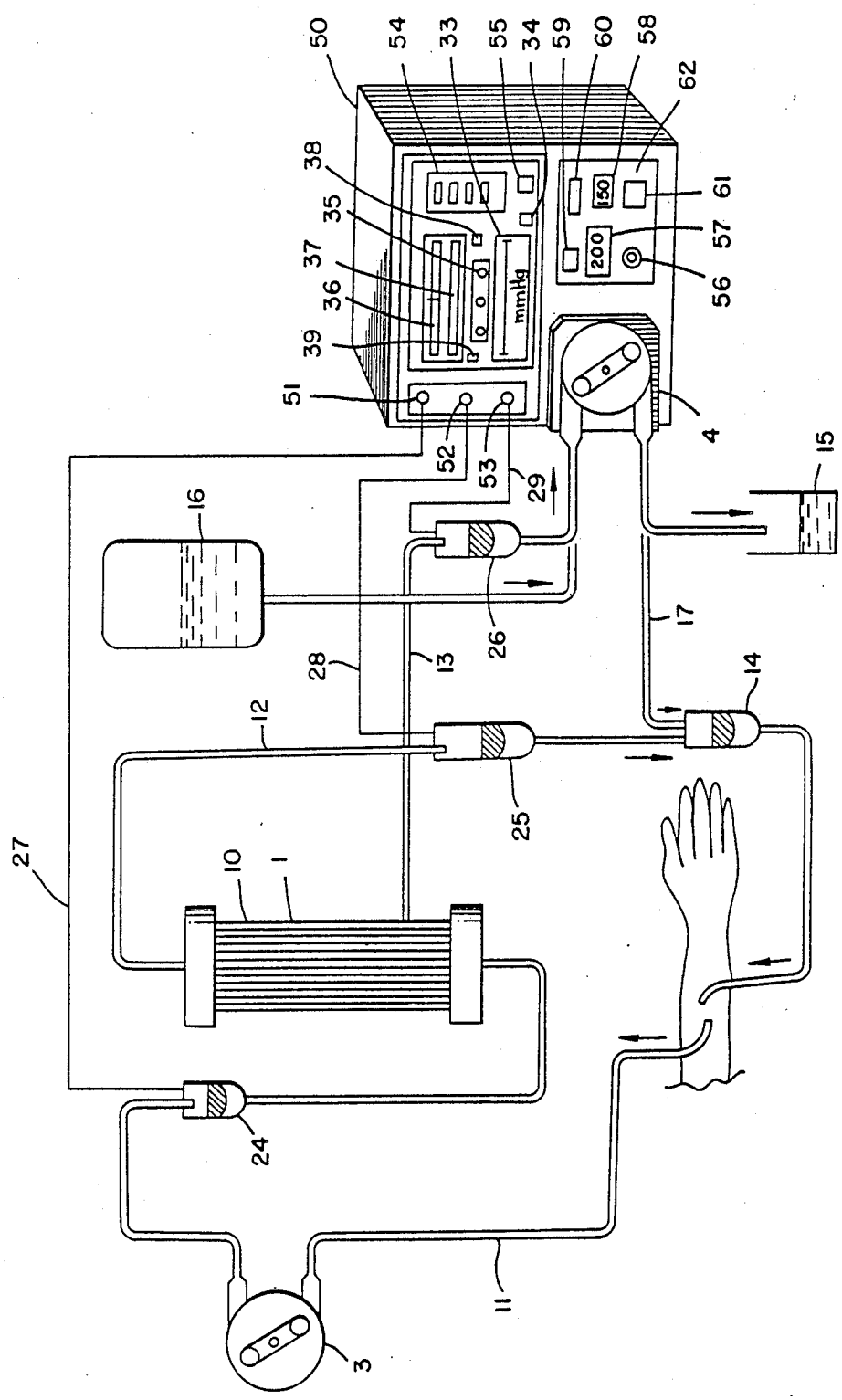
FIG. 4 is a block diagram showing an extracorporeal circulation blood circuit employing the apparatus of the invention.

FIG. 4 illustrates an example in which the plasma separation apparatus is employed in separating blood into plasma and corpuscular components and in which the plasma fraction is discharged and the corpuscular components, mixed with a plasma preparation of same quantity as the discharged plasma, are returned to the intracorporeal circulation. In this instance, blood led from a patient's artery into a blood transfer tube is supplied by means of a roller pump 3 to a plasma separator 1 incorporating hollow fibers 10. The blood is separated by the hollow fibers into plasma and corpuscular components. In a chamber 14, disposed in a corpuscular component transfer tube 12, are the corpuscular components mixed with a plasma preparation to be hereinafter described, for subsequent return to the intracorporeal circulation. Led into a plasma transfer tube 13 by a dual-type plasma pump 4, the plasma fraction is discharged into a vessel 15. The plasma preparation held in a bag 16, is fed through a plasma preparation transfer tube 17 into the chamber 14 in the same quantity as the plasma pumped out by the dual-type plasma pump 4. Said transfer tubes 11, 12, 13 are fitted respectively with air chambers 24, 25, 26 for pressure detection. Pressure sensing tubes 27, 28, 29 open into the upper spaces of the individual air chambers. These sensing tubes 27, 28, 29 are connected respectively to an arterial pressure connector 51, a venous pressure connector 52, and a filtration pressure connector 53. These connectors, in turn, are connected to pressure sensors disposed in a box 50 housing a trans-membrane pressure control circuit 5 and the dual-type plasma discharge pump 4. On the upper portion of front panel of said box 50 there are disposed, in addition to said connectors 51, 52, 53, an analog-meter type pressure indicator 33, a changeover switch 34 for selection of pressure indication as to said three pressure types, three lamps 35 for pressure indication as selected by the changeover switch, and a trans-membrane pressure differential display 36 and a trans-membrane pressure differential setting display 37, both being of a multi bar-graph type using a luminescent semiconductor diode and adapted to give indications by color classification, i.e., green, orange and red, for each five dots. Said trans-membrane pressure differential display is such that if, for example, the green zone stands for less than 50 mmHg, the orange zone for 50–100 mmHg, and the red zone for over 100 mmHg, then the green may be classified as safety zone, the orange as hazardous zone, and the red as abnormal zone. Such trans-membrane pressure differential display is convenient because it facilitates acknowledgement as to whether or not the apparatus is operating with a normal trans-membrane pressure differential. Numeral 38 is a set-pressure UP switch for trans-membrane pressure differential. Numeral 39 is a set-pressure DOWN switch. These switches 38, 39 permit easy setting of transmembrane pressure differential. Furthermore, there is provided an alarm lamp 54 which indicates a cause or causes (e.g. arterial pressure, veinous pressure, filtration pressure, trans-membrane pressure differential) of any abnormal pressure caused during operation, and a checking switch for checking to see that any abnormal condition has been corrected. On the lower portion of front panel of the box there are disposed, besides the dual-type roller pump 4, a dial 56 for setting the number of revolutions of the roller pump, a digital-type plasma discharge rate display 57, a discharged-plasma total quantity display 58, a total quantity reset switch 62, an automatic switch 59 for actuating an automatic control function for trans-membrane pressure differential, a lamp 60 for indicating that the number of revolutions of the pump is being decreased, and a power switch 61. The apparatus is operated with the automatic switch ON.

During operation, if indicated pressure as to trans-membrane pressure differential is in excess of the set pressure, lamp 60 lights to show that the number of revolutions of the pump is being lowered; the number of revolutions is gradually lowered relative to the value set by the pump flow-rate setting dial 56. The flow rate of plasma is lowered as the number of revolutions of the pump. Accordingly, pressure indication as to trans-membrane pressure is also lowered. If such pressure indication is lowered to a level below the preset pressure, the lamp 60 indicating the number of pump revolutions being decreased is put out, and the number of revolutions of the pump at that time is maintained as it is. If the automatic switch 59 is turned OFF, the pump is allowed to run at the number of revolutions set by the flow rate setting dial 56. (Even if pressure indication as to trans-membrane pressure differential is in excess of the preset value, the number of revolutions of the pump is not decreased.)

The above described apparatus may be employed in the following manner. The plasma separator 1 and the individual transfer tubes 11, 12, 13, 17 are attached to pumps 3, 4, and the pressure sensing tubes 27, 28, 29, attached to the air chambers 24, 25, 26, are connected to the individual connectors 51, 52, 53. Then, 1. Washing
   (1) Power switch 61 is turned ON.
   (2) Before put in clinical use, the plasma separator and transfer tubes are washed with physiological salt water (1000 ml), and at the same time, bubbles present in each transfer tube are expelled in order to prevent bubble entry into a living body.
2. Clinical use
   (1) The bag 16 containing a plasma preparation is set in place.
   (2) Upper and lower limits for artery and filtration pressure and trans-membrane pressure differential are set at suitable values. Concurrently, the automatic switch may be depressed to position so that automatic control function works to inhibit hemolytic activity.
   (3) A transfer tube is connected to the patient to form an extracorporeal circulation circuit. The blood pump 3 is operated to circulate blood at a flow rate of about 100 ml/min.
   (4) flow-rate setting knob 56 is controlled to separate plasma (Complemental plasma preparation) at a flow rate of about 20 ml/min. Simultaneously with start of plasma separation, total quantity indicator 58 is set to zero by total quantity reset switch 62.
   (5) When the total quantity indicator 58 (treated quantity of plasma) indicates that the predetermined value has been reached, autotransfusion is effected of blood and plasma present in the transfer tube and plasma separator, and power switch 61 is turned off.
3. After clinical use
   (1) The plasma separator and transfer tube are removed and discarded.

When separating blood into plasma and corpuscular components, if the plasma separating operation is carried out under the condition of the blood side pressure being low, the plasma discharge pressure may act as a negative pressure to destroy the corpuscular components. Therefore, it is desirable to control the plasma discharge pressure so that said pressure will not destroy the corpuscular components.

Figure 5:
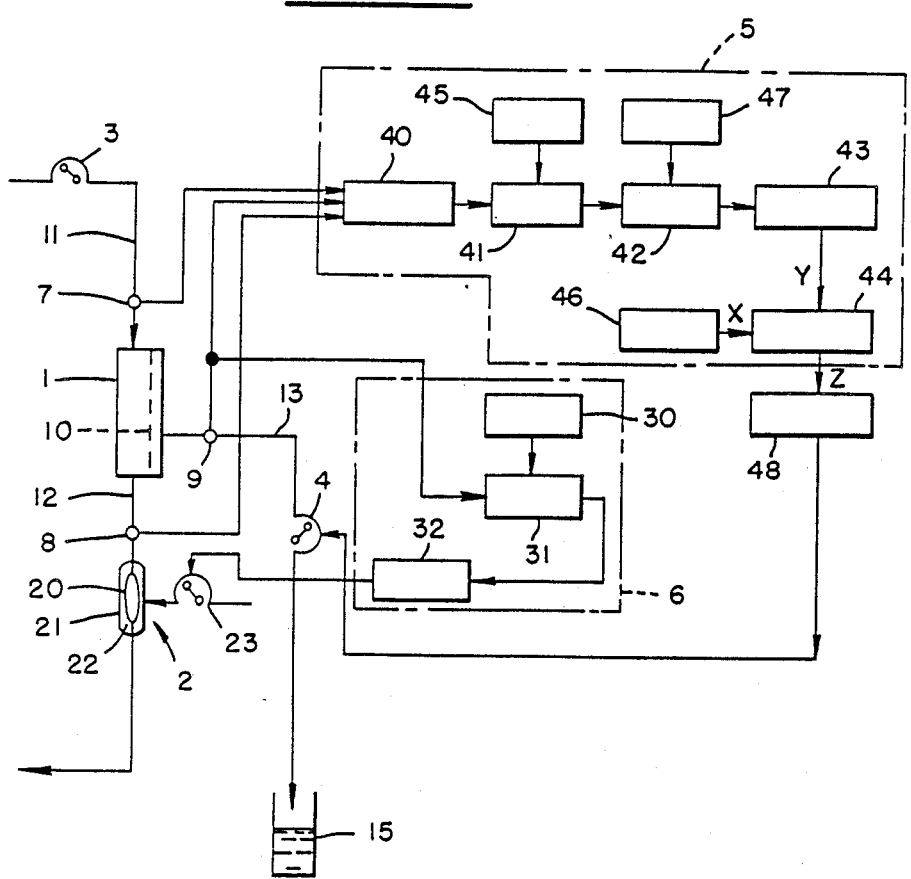
FIG. 5 is an electric circuit diagram showing another embodiment of the invention.

FIG. 5 shows, by way of example, means for simultaneously controlling two pressures, that is, said trans-membrane pressure differential and plasma discharge pressure. Said means comprise a pressure control valve 2 and a plasma discharge pressure control circuit 6.

Figure 6:
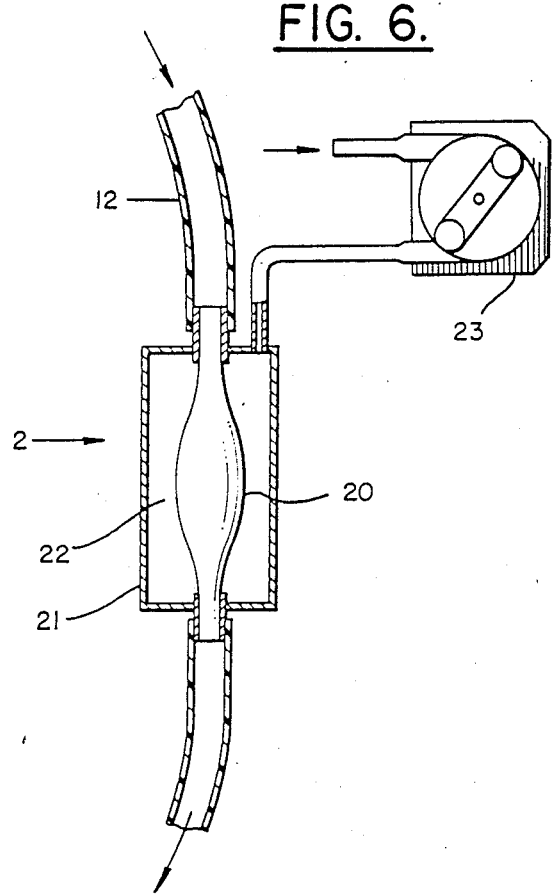
FIG. 6 is a sectional view showing a pressure control valve.

The pressure control valve 2, provided in said corpuscular component transfer tube 12, is preferably a pinch valve of such construction that will not damage the corpuscular components. For example, such pinch valve as FIG. 6 illustrates, may preferably comprise a flexible, corpuscular component circulating member 20 in sheet or tube form of such flexible material as silicone rubber, polyurethane, flexible polyvinyl chloride, or natural or synthetic rubber, a case 21 enclosing said member 20 and made of such non-flexible material as polypropylene, polyethylene, rigid polyvinyl chloride, polycarbonate or the like, and a closed chamber 22 defined by and between said circulating member 20 and said case 21. Said valve is designed so that a pressurized fluid is supplied by pressurized-fluid supply means 23 into the closed chamber so as to shut off the blood circulating member 20. As pressurized fluid supply means may be employed, a pump or compressor which will supply liquid or gas into the closed chamber. More specifically, positive displacement pumps, such as a roller pump or a plunger pump, are preferable because they can maintain pressure condition when operation is stopped. Above all, a multi-roller type roller pump is most practical which involves less pulsation during pressure application. For fluid supplied by means of pressurized fluid supply means are preferable such fluids as air, physiological salt solution, dextrose liquid, which involves no danger if the corpuscular component circulating member 20 is damaged so that the fluid leaks and flows toward the corpuscular component side. More particularly, air is convenient for use, since it only required that the suction port of the pump is left open. For this purpose, it is desirable that a germ-expelling filter is attached to the suction port.

The plasma discharge pressure control circuit 6 is such that if the plasma discharge pressure is lowered to a level below the preset pressure, the pressure control valve 2 is throttled for adjustment. It comprises a pressure setting unit 30, a comparator circuit 31, and a motor drive 32. Said control circuit 6 compares a preset pressure value from the pressure setting unit 30 and a detected pressure value from the pressure sensor 9 which detects plasma discharge pressures, such comparison being performed at the comparator circuit 31, and if the detected pressure value is smaller than the preset pressure value, an output is applied to the drive unit 32 to actuate a motor of the pressurized fluid supply pump 23. When pressurized air is supplied by said pump 23 into the closed chamber 22 of the pressure control valve, the pressure control valve 2 is throttled and accordingly the blood side pressure in the plasma separator 1 is increased so that the plasma discharge pressure is increased.

Pressure setting at said pressure setting unit 30 can be freely made within the range of about $-50$ to about $+100$ mmHg, but usually pressure is set in a low positive pressure range, that is, about 0 to about 20 mmHg. Control of plasma discharge pressures is carried out in the following manner.

When a plasma discharge pressure is detected by the pressure sensor 9, a detection signal is transmitted to the plasma discharge pressure control circuit 6. In said control circuit 6, a comparison is made of said detected value and the preset pressure value set by the pressure setting circuit 30 (e.g., set within the range of about 0–20 mmHg) through the comparator circuit 31, and if the detected value is smaller than the preset value, an instruction signal is issued to the motor drive unit 32 to cause it to actuate the pressurized fluid supply pump 23 of the pressure control valve 2. Such signal continues to be sent until the difference between the detected value and the preset value is reduced to zero.

Through operation of the pump 23, pressurized fluid is supplied into the closed chamber 22 of the pressure control valve 2. As pressure increases in the closed chamber 22, the corpuscular-component circulating member 20 of flexible material is pressed and as a result the corpuscular component transfer tube is throttled. The blood side pressure in the plasma separator 1 is increased and the plasma discharge pressure is proportionally increased. If the plasma discharge pressure is restored to a level above the preset value, then said instruction signal is ceased and operation of the pump 23 is stopped. For this purpose, there may be provided a circuit which permits the pressure pump to stop after restoring a plasma discharge pressure slightly biased rather than that at the start of pump operation, whereby it is possible to obtain more stable operation, that is, operation less subject to the influence of pulsed plasma discharge pressure.

Said trans-membrane pressure differential control circuit and said plasma discharge pressure control circuit, each may be operated independently of or concurrently with the other.

As above described, the apparatus of the invention has an outstanding advantage that good membrane permeability to plasma is assured without damage to the blood by controlling the trans-membrane pressure differential within a predetermined range and that good membrane performance can be obtained by controlling the rate of plasma discharge according to the decrease in the membrane permeability. Furthermore, the apparatus according to the invention can be advantageously employed in various treatments referred to above, such as those intended for separating plasma and corpuscular components to remove the plasma fraction containing unfavorable factors, or to remove unfavorable factors from the plasma fraction.

The patents and patent applications set forth in this application are intended to be incorporated in their entireties by reference herein.

It is apparent that there has been provided in accordance with this invention an apparatus and method for plasma separation which satisfies the objects, means, and advantages set forth hereinabove. While the invention has been described in combination with the embodiments thereof, it is evident that many alternatives, modifications, and variations will be apparent to those skilled in the art in light of the foregoing description. Accordingly, it is intended to embrace all such alternatives, modifications, and variations as fall within the spirit and broad scope of the appended claims.

What is claimed is:

1. The process of plasma separation, comprising the steps of:
    delivering blood comprising plasma and corpuscular components through a blood transfer tube to the blood inlet of a plasma separator incorporating a membrane separating the plasma separator into a filtering side and a filtrate side, said membrane having pores of a size which prevents permeability by the corpuscular components and which enables permeability of the plasma;
    separating the blood from the filtering side of said plasma separator with said membrane into plasma for discharge from the filtrate side through a plasma outlet and corpuscular components for discharge from the filtering side through a corpuscular component outlet;
    discharging plasma from the plasma outlet with a plasma pump via a plasma transfer tube;
    measuring the pressure $P_1$ of blood at the blood inlet;
    measuring the pressure $P_2$ of the corpuscular components at the corpuscular component outlet;
    measuring the pressure $P_3$ of the plasma at the plasma outlet;
    the step of separating the blood including the steps of:
    selecting a predetermined transmembrane pressure differential above which hemolysis of the corpuscular components is likely;
    determining a detected transmembrane pressure differential $P_T$ using the measured pressures $P_1$, $P_2$ and $P_3$ according to the equation:

$$P_T = \frac{P_1 + P_2}{2} - P_3$$

comparing the detected transmembrane pressure differential to the predetermined transmembrane pressure differential; and setting the number of revolutions of the plasma pump to a predetermined value, said predetermined value being below a maximum value of revolutions of the plasma pump corresponding to the maximum plasma discharge rate of the membrane;

adjusting the transmembrane pressure differential to a level below the predetermined transmembrane pressure differential if the detected transmembrane pressure differential is greater than the predetermined transmembrane pressure differential; and the step of adjusting the transmembrane pressure differential including the step of decreasing the number of revolutions of the plasma pump equal to a speed drop value to a value which maintains the detected transmembrane pressure differential below the predetermined transmembrane pressure differential; said step of decreasing the number of revolutions including the step of subtracting the revolutions of the plasma pump equal to the speed drop value from the predetermined value.

2. The process of claim 1 further including the step of maintaining the number of revolutions of the plasma pump at said value.

3. The process of claim 2 including the steps of:
withdrawing blood from a donor through a blood transfer tube; and
returning the separated corpuscular component from the corpuscular component outlet to the donor.

4. The process of claim 1 including the steps of:
selecting a predetermined plasma discharge pressure;
regulating the pressure $P_2$ at the corpuscular component outlet;
controlling plasma discharge pressure $P_3$ by regulating pressure $P_2$ until the pressure differential between the measured plasma discharge pressure and the predetermined plasma discharge pressure reaches zero if the measured plasma discharge pressure is smaller than the predetermined plasma discharge pressure.

5. The process of claim 4 wherein the step of regulating the pressure at the corpuscular component outlet includes the steps of:
providing a pressure control valve connected to the corpuscular component outlet; and
throttling the control valve to increase the pressure on the filtering side of the plasma separator whereby the plasma discharge pressure is proportionally increased.

6. The process of claim 5 including the step of ceasing regulation of the pressure at the corpuscular component outlet when the plasma discharge pressure is restored to a value above the predetermined discharge pressure.

7. An article of manufacture constructed in accordance with the process of claim 1.

8. An article of manufacture constructed in accordance with the process of claim 1.

9. The process of plasma separation, comprising the steps of:
delivering blood comprising plasma and corpuscular components through a blood transfer tube to the blood inlet of a plasma separator incorporating a membrane separating the plasma separator into a filtering side and a filtrate side, said membrane having pores of a size which prevents permeability by the corpuscular components and which enables permeability of the plasma;
separating the blood from the filtering side of said plasma separator with said membrane into plasma for discharge from the filtrate side through a plasma outlet and corpuscular components for discharge from the filtering side through a corpuscular component outlet;
discharging plasma from the plasma outlet with a plasma pump via a plasma transfer tube;
measuring the pressure $P_1$ of blood at the blood inlet;
measuring the pressure $P_3$ of the plasma at the plasma outlet;
the step of separating the blood including the steps:
of selecting a predetermined transmembrane pressure differential above which hemolysis of the corpuscular components is likely;
determining a detected transmembrane pressure differential $P_T$ using the measured pressures $P_1$ and $P_3$ according to the equation:

$P_T = P_1 - P_3$ comparing the detected transmembrane pressure differential to the predetermined transmembrane pressure differential; and
setting the number of revolutions of the plasma pump to a predetermined value, said predetermined value being below a maximum value of revolutions of the plasma pump corresponding to the maximum plasma discharge rate of the membrane;
adjusting the transmembrane pressure differential to a level below the predetermined transmembrane pressure differential if the detected transmembrane pressure differential is greater than the predetermined transmembrane pressure differential; and
the step of adjusting the transmembrane pressure differential including the step of decreasing the number of revolutions of the plasma pump equal to a speed drop value to a value which maintains the detected transmembrane pressure differential below the predetermined transmembrane pressure differential; said step of decreasing the number of revolutions including the step of subtracting the revolutions of the plasma pump equal to the speed drop value from the predetermined value.

10. The process of claim 9 including the steps of:
selecting a predetermined plasma discharge pressure;
measuring the pressure $P_2$ at the corpuscular component outlet;
regulating the pressure $P_2$;
controlling plasma discharge pressure by regulating pressure $P_2$ until the pressure differential between the measured plasma discharge pressure and the predetermined plasma discharge pressure reaches zero if the measured plasma discharge pressure is smaller than the predetermined plasma discharge pressure.

11. The process of claim 10 wherein the step of regulating the pressure at the corpuscular component outlet includes providing a pressure control connected to the corpuscular component outlet; and
throttling the control valve to increase the pressure on the blood side of the plasma separator whereby the plasma discharge pressure is proportionally increased.

12. An article of manufacture constructed in accordance with the process of claim 9.

13. An article of manufacture constructed in accordance with the process of claim 10.

14. An apparatus for plasma separation, comprising:
means for delivering blood comprising plasma and corpuscular components through a blood transfer tube to the blood inlet of a plasma separator incorporating a membrane separator into a filtering side and a filtrate separating the plasma side, said membrane having pores of a size which prevents permeability by the corpuscular components and which enables permeability of the plasma;
means for separating the blood from the filtering side of said plasma separator with said membrane into plasma for discharge through a plasma outlet and corpuscular components for discharge from the filtrate side through a corpuscular component outlet;
means for discharge plasma from the plasma outlet with a plasma pump via a plasma transfer tube;
means for measuring the pressure $P_1$ of blood at the blood inlet;
means for measuring the pressure $P_2$ of the corpuscular components at the corpuscular component outlet;
means for measuring the pressure $P_3$ of the plasma at the plasma outlet;
said means for separating the blood, including:
means for selecting a predetermined transmembrane pressure differential above which hemolysis of the corpuscular components is likely;
means for determining a detected transmembrane pressure differential $P_T$ using the measured pressures $P_1$, $P_2$ and $P_3$ according to the equation:

$$P_T = \frac{P_1 + P_2}{P_2} - P_3$$

means for comparing the detected transmembrane pressure differential to the predetermined transmembrane pressure differential; and
means for setting the number of revolutions of the plasma pump to a predetermined value, said predetermined value being below a maximum value of revolutions of the plasma pump corresponding to the maximum plasma discharge rate of the membrane;
means for adjusting the transmembrane pressure differential to a level below the predetermined transmembrane pressure differential if the detected transmembrane pressure differential is greater than the predetermined transmembrane pressure differential; and
the means for adjusting the transmembrane pressure differential including:
means for decreasing the number of revolutions of the plasma pump equal to a speed drop value to a value which maintains the detected transmembrane pressure differential below the predetermined transmembrane pressure differential, the means for decreasing the number of revolutions including means for subtracting the revolutions of the plasma pump equal to the speed drop value from the predetermined value.

15. The apparatus of claim 14 further including means for maintaining the number of revolutions of the plasma pump at said value.

16. The apparatus of claim 15 including:
means for withdrawing blood from a donor through a blood transfer tube; and
means for returning the separated corpuscular component from the corpuscular component outlet to the donor.

17. The apparatus of claim 14 including:
means for selecting a predetermined plasma discharge pressure;
means for regulating the pressure $P_2$ at the corpuscular component outlet;
means for controlling plasma discharge pressure $P_3$ by regulating pressure $P_2$ until the pressure differential between the measured plasma discharge pressure and the predetermined plasma discharge pressure reaches zero if the measured plasma discharge is smaller than the predetermined plasma discharge pressure.

18. The apparatus of claim 17 wherein the means for regulating the pressure at the corpuscular component outlet includes:
a pressure control valve connected to the corpuscular component outlet; and
means for throttling the control valve to increase the blood pressure on the filtering side of the plasma separator whereby the plasma discharge pressure is proportionally increased.

19. The apparatus of claim 18 including means for ceasing regulation of the pressure at the corpuscular component outlet when the plasma discharge pressure is restored to a value above the predetermined discharge pressure.

20. The apparatus of claim 18 means for ceasing regulation of the pressure at the corpuscular component outlet when the plasma discharge pressure is restored to a value above the predetermined discharge pressure.

21. An apparatus for plasma separation, comprising:
means for delivering blood comprising plasma and corpuscular components through a blood transfer tube to the blood inlet of a plasma separator incorporating a membrane separating the plasma separator into a filtering side and a filtrate side, said membrane having pores of a size which prevents permeability y the corpuscular components and which enables permeability of the plasma;
means for separating the blood from the filtering side of said plasma separator with said membrane into plasma for discharge through a plasma outlet and corpuscular components for discharge from the filtrate side through a corpuscular component outlet;
means for discharging plasma from the plasma outlet with a plasma pump via a plasma transfer tube;
means for measuring the pressure $P_1$ of blood at the blood inlet;
means for measuring the pressure $P_3$ of the plasma at the plasma outlet;
said means for separating the blood, including;
means for selecting a predetermined transmembrane pressure differential above which hemolysis of the corpuscular components is likely;
means for determining a detected transmembrane pressure differential $P_T$ using the measured pressures $P_1$ and $P_3$ according to the equation:

$P_T = P_1 - P_3$ means for comparing the detected transmembrane pressure differential to the predetermined transmembrane pressure differential; and means for setting the number of revolutions of the plasma pump to a predetermined value, said predetermined value being below a maximum value of revolutions of the plasma pump corresponding to the maximum plasma discharge rate of the membrane;

means for adjusting the transmembrane pressure differential to a level below the predetermined transmembrane pressure differential if the detected transmembrane pressure differential is greater than the predetermined transmembrane pressure differential; and the means for adjusting the transmembrane pressure differential including:

means for decreasing the number of revolutions of the plasma pump equal to a speed drop value to a value which maintains the detected transmembrane pressure differential below the predetermined transmembrane pressure differential, the means for decreasing the number of revolutions including the step of subtracting the revolutions of the plasma pump equal to the speed drop value from the predetermined value.

22. The apparatus of claim 21 including:

means for selecting a predetermined plasma discharge pressure;

means for measuring the pressure $P_2$ at the corpuscular component outlet;

means for regulating the pressure $P_2$;

means for controlling plasma discharge pressure $P_3$ by regulating pressure $P_2$ until the pressure differential between the measured plasma discharge pressure and the predetermined plasma discharge pressure reaches zero if the measured plasma discharge is smaller than the predetermined plasma discharge pressure.

23. The apparatus of claim 22 wherein the means for regulating the pressure at the corpuscular component outlet includes:

a pressure control valve connected to the corpuscular component outlet; and means for throttling the control valve to increase the blood pressure on the filtering side of the plasma separator whereby the plasma discharge pressure is proportionally increased.

* * * * *

UNITED STATES PATENT AND TRADEMARK OFFICE
CERTIFICATE OF CORRECTION

PATENT NO. : 4,936,980

DATED : June 26, 1990

INVENTOR(S) : Y. Harada, et al

It is certified that error appears in the above-identified patent and that said Letters Patent is hereby corrected as shown below:

In Claim 8, line 2 of the patent, "1" should read --4--,

In Claim 14, lines 5-6 of the patent, "separator into a filtering side and a filtrate separating the plasma side," should read --separating the plasma separator into a filtering side and filtrate side, --.

In Claim 20, line 1, "18" should read --23--.

Signed and Sealed this

Tenth Day of September, 1991

Attest:

HARRY F. MANBECK, JR.

Attesting Officer

Commissioner of Patents and Trademarks